United States Patent [19]

Shibata

[11] 4,382,887
[45] May 10, 1983

[54] NOVEL GLYCOPEPTIDE AND METHODS OF ISOLATING AND USING THE SAME

[76] Inventor: Seiichi Shibata, 40-11, Takatanobaba 4-chome, Shinjuku-ku, Tokyo, Japan

[21] Appl. No.: 165,602

[22] Filed: Jul. 3, 1980

[30] Foreign Application Priority Data

Sep. 26, 1979 [JP] Japan .................. 54-123669

[51] Int. Cl.³ .................. A61K 49/00; C07C 103/52; C07G 7/00
[52] U.S. Cl. .................. 260/112.5 R; 424/9; 424/95; 424/99; 424/103; 424/177; 424/180; 536/1.1
[58] Field of Search .................. 260/112.5 R; 424/9, 424/95, 99, 103, 177, 180; 536/1

[56] References Cited

PUBLICATIONS

Shibata, Biochim et Biophy. Acta, vol. 499, 1977 pp. 392-403.
Shibata, Chem. Abs., vol. 86, 1977 Ab. No. 86:53552p.
Shibata, The J. of Immunol. vol. 106, May 1971 p. 1284.
Shibata, The J. of Immunol. vol. 102, 1969 pp. 593-601.
Shibata, The J. of Immunol. vol. 104, 1970 pp. 215-223.
Shibata, Japan. J. Exp. Med. vol. 37, No. 4, 1967 pp. 337-353.
Shibata, Carbohydrate Res. vol. 81, 1980 pp. 345-348.
Shibata, Carbohydrate Res. vol. 86, 1980 pp. 316-320.
Spiro, The J. Biol. Chem., vol. 242, 1967 pp. 1923-1932.
Shibata, Japan Medical Res. Foundation Pub. vol. 7, (Glomerulonephritis) 1979 pp. 23-38.
Nagasawa, Supra p. 39.
Shibata, Nephron, vol. 16, 1976 pp. 241-255.

*Primary Examiner*—Anna P. Fagelson
*Attorney, Agent, or Firm*—Oldham, Oldham, Hudak, Weber & Sand, Co.

[57] ABSTRACT

A novel glycopeptide is disclosed, which consists of a sugar moiety having a structural formula

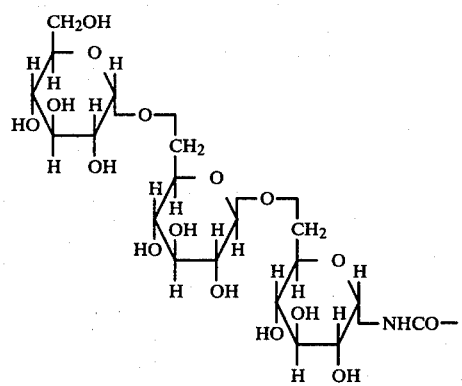

and a peptide moiety linking to the sugar moiety through N-glycoside bond. The glycopeptide is isolated from organs of normal animals, especially kidney, or urine from healthy human being, and has a biological activity of inducing lesions of kidney in animals. The lesions of kidney induced by an injection of the glycopeptide are very similar to spectrum of human glomerulonephritis. Accordingly, an experimental model for study on human glomerulonephritis is established.

6 Claims, 4 Drawing Figures

NOVEL GLYCOPEPTIDE AND METHODS OF ISOLATING AND USING THE SAME

BACKGROUND OF THE INVENTION

The present invention relates to a novel glycopeptide consisting of a sugar moiety having a structural formula

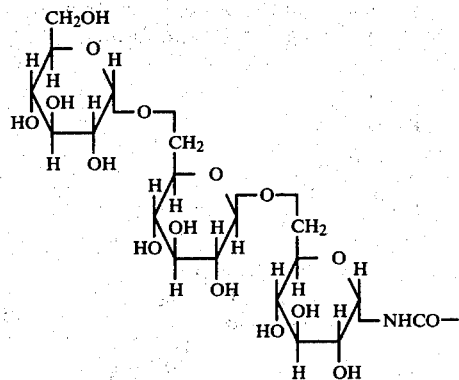

and a peptide moiety linking to the sugar moiety through N-glycoside bond and a process of isolating it. The present invention relates also to an agent of inducing glomerulonephritis in an animal and to a method of preparing an experimental model for study on human glomerulonephritis.

It is very important in medical and pharmaceutical fields, especially for an development of therapeutic treatment of human disease, screening of medicines or the like, to prepare stably, plentifully and economically an experimental model, in other words, an experimental animal having lesions which are strikingly similar to spectrum of human disease. Recently, the supply of experimental models such as, for example, rat with hypertension, mouse with diabetes, rat with digestive ulcer or the like has contributed remarkably to the development of therapeutic treatments.

Although, with respect to human glmerulonephritis, many experimental models have been reported, most of them are those about acute glomerulonephritis and have only a similarity in morphologic changes but no similarity in clinical functions such as metabolism, etc. Therefore, they cannot be utilized for the developments of diagnosis and therapeutic agents.

It is well known that there is Masugi's glomerulonephritis as one of the experimental models. Masugi's glomerulonephritis is such phenomenon that glomerulonephritis is induced accompanying with proteinuria by injecting a serum which is obtainable from steps of (1) injecting a homogenate of kidney excised from normal animal to heterologous animal in the rate of one or two times a week for about 2 months, of (2) collecting blood from the animal and of (3) separating the serum from the blood, to a normal animal homologous to the animal from which kidney is excised. As apparent from the course of inducing glomerulonephritis, it has been believed that Masugi's glomerulonephritis is induced through anitgen-antibody reaction using the homogenate of kidney.

Thereafter, many attempts have been made for purifying the homogerate to isolate a complete antigen substance that prepares "nephrotoxic antiserum" having an ability to induce glomerulonephritis. As the results of anatomical attempts, it has been found that the complete antigen substance is mainly present in glomerulus of kidney, especially glomerular basement membrane (GBM). Although many attempts from the point of chemistry have been made, the complete antigen substance has not been made clear yet.

Spiro reported that two glycopeptides can be isolated from bovine GBM [Spiro, R. G., "J. Biol. Chem.", Vol. 242, No. 8, 1923–1932 (1967)].

Spiro's procedure for isolating the two glycopeptides is as follows. Firstly, GBM is separated from kidney according to Krakower and Greenspon's method [Krakower and Greenspon "Arch. Path" 51, 629–639, (1951)]. The separated GBM is dispersed in 0.1 M Tris acetate buffer and digested with collagenase at pH of 7.4 and temperature of 37° C. The supernatant liquid obtainable from centrifuging the digestion solution is conditioned at pH 7.8 and then is digested with pronase at 37° C. Thus digestion solution is centrifuged to collect the supernatant liquid.

The supernatant liquid thus obtained is fractionated with Sephadex G-25. As shown in FIG. 1 of the literature mentioned above, two fractions which have sugar peaks 1 and 2 (by anthrone) respectively are obtained by this fractionation. The fraction (sugard peak 1) belonging to the void volume of Sephadex G-25 is further fractionated with Sephadex G-50. As shown in FIG. 5 of the literature mentioned above, sugar peak 1 is divided into two sugar peaks (by anthrone), one of them belonging to the void volume of Sephadex G-50.

Spiro found from this procedure two glycopeptides from the sugar peak 2 in FIG. 1 and the right sugar peak in FIG. 5. The glycopeptide of the sugar peak 2 is disaccharide comprising glucose and galactose in the ratio of 1:1 and one molecule of hydroxylysin, while the glycopeptide of the another sugar peak is heteropolysaccharide comprising galactose, mannose, glucosamine and fucose. However, both of them have no biological activity.

Spiro discarded the left sugar peak in FIG. 5 as impurities according to the common knowledge in this field because it belongs to the void volume.

The inventor has studied an establishment of an experimental model for human glomerulonephritis, especially for adult human glomerulonephritis.

It was found surprisingly that there is contained a substance having an ability to induce glomerulonephritis in animal in the left sugar peak in FIG. 5 which has been discarded by Spiro and that this substance is different quite from the two glycopeptides isolated by Spiro. It was found also that the biological activity of glycopeptide of the present invention is displayed by injecting the glycopeptide directly to an animal.

The inventor termed such biological activity of the glycopeptide of the present invention "nephrotogenicity" against that the biological activity in Masugi's glomerulonephritis was termed "nephrotoxicity".

STATEMENT OF OBJECTS

It is an object of the present invention to provide a novel glycopeptide consisting of a sugar moiety having a stractural formula

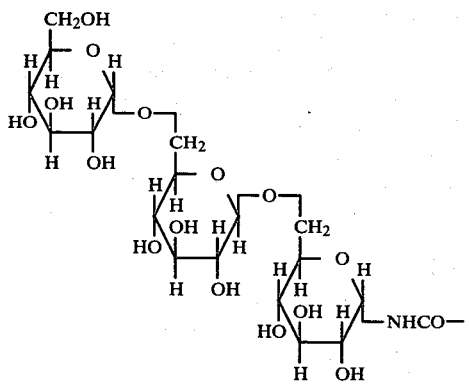

and a peptide moiety linking to the sugar moiety through N-glycoside bond.

It is another object of the present invention to provide a process of isolating the glycopeptide, comprising steps of (1) digesting an organ of normal animal with a protein-digesting enzyme and centrifuging, of (2) digesting the supernatant liquid obtained in the step (1) with pronase and centrifuging, of (3) dialyzing the supernatant liquid obtained in the step (2), of (4) treating the non-dialyzable substance with trichloroacetic acid and centrifuging, and of (5) contacting the supernatant liquid obtained in the step (4) with concanavalin A and eluting the substance trapped on concanavalin A.

It is another object of the present invention to provide a process of isolating the glycopeptide, comprising steps of (1) digesting an organ of normal animal with a protein-digesting enzyme and centrifuging, of (2) digesting the supernatant liquid obtained in the step (1) with pronase and centrifuging, of (3) dialyzing the supernatant liquid obtained in the step (2), of (4) treating the non-dialyzable substance with trichloroacetic acid and centrifuging, and of (5) contacting the supernatant liquid obtained in the step (4) with non-water soluble material having negative charge and eluting the substance adsorbed on the non-water soluble material.

It is another object of the present invention to provide a process of isolating the glycopeptide comprising steps of (1) contacting urine from healthy human being or the concentrate thereof with non-water soluble material having negative charge and eluting substances adsorbed on the non-water soluble material, of (2) digesting the eluate with pronase and centrifuging, of (3) dialyzing the supernatant liquid obtained in the step (2), and of (4) treating the non-dialyzable substance with trichloroacetic acid.

It is another object of the present invention to provide an agent of inducing glomerulonephritis in an animal characterized in that it contains the glycopeptide as an active component.

It is still another object of the present invention to provide a method of preparing an experimental model useful for study on human glomerulonephritis characterized in that the glycopeptide is injected to an experimental animal to induce lesions similar to those of human glomerulonephritis.

DETAILED DESCRIPTION OF INVENTION

The glycopeptide of the present invention consists of a sugar moiety having a structural formula

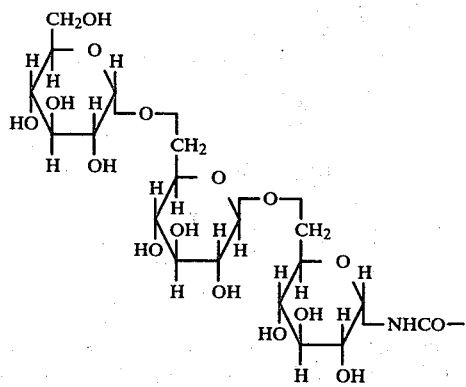

and a peptide moiety linking to the sugar moiety through N-glycoside bond.

This glycopeptide is characterized not only by novel structure of the sugar moiety but also by unique property. In other words, while Masugi's glomerulonephritis is induced through the antigen-antibody reaction, glomerulonephritis in the case of the present invention, is induced by a single injection in hind footpad of the animal and the induced glomerulonephritis makes progress to chronic glomerulonephritis (contracted kidney) after 6–8 months from the injection.

The nephritogenicity of the glycopeptide is derived from the sugar moiety. More detailedly, it was confirmed that although even if the peptide moiety is destroyed by suitable means such as digestion with trypsin or collagenase and pronase, the nephritogenicity is not damaged at all, when the sugar moiety is destroyed by $IO_4$ oxidation, glomerulonephritis is not induced at all.

Now, the determination of structure of the sugar moiety which controls the nephritogenicity will be detailed hereinafter.

i. consisting of glucose only

Figure 1:
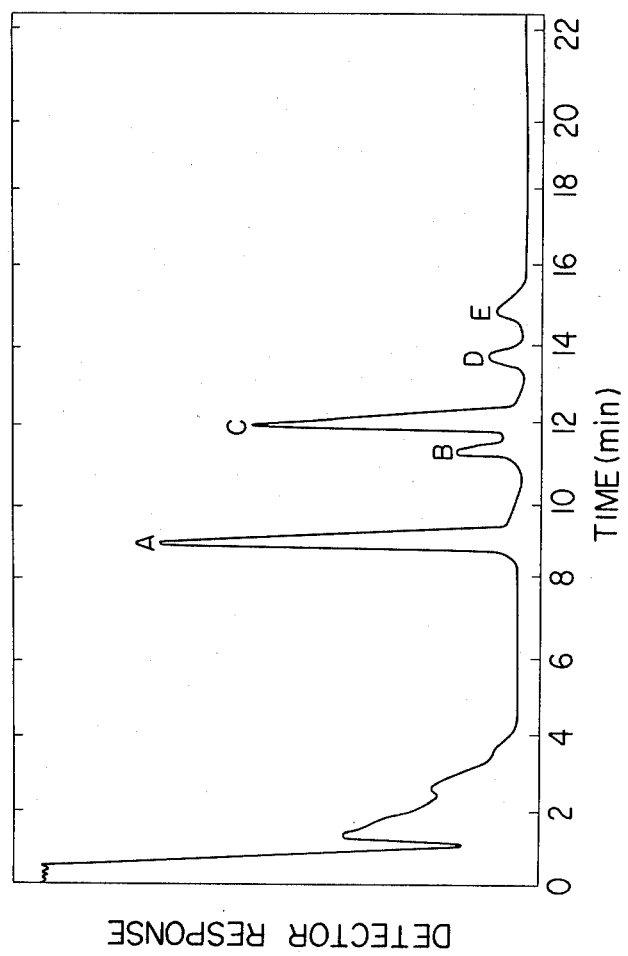
FIG. 1 is a gas-chromatographic chart of a product obtainable from methylation of the glycopeptide of the present invention.

According to usual method in the determination of structure of sugar [Hakomori, S. J. Biochem. 55, 205–208, (1964)], the glycopeptide sample isolated from rat GBM was methylated and the methylated product was subjected to gas-chromatography. FIG. 1 shows the obtained gas-chromatographic spectrum. The compounds in the peaks of the spectrum were identified by Mass spectrometory. The obtained results were reported in Table.

TABLE

| peak | compound |
|------|----------|
| A | 2,3,4,6-tetra-O—methyl-D-glucose |
| B | 3,4,6-tri-O—methyl-D-glucose |
| C | 2,3,6- and 2,3,4-tri-O—methyl-D-glucose |
| D | 3,6-di-O—methyl-D-glucose |
| E | 2,4-di-O—methyl-D-glucose |

As the results, it was found that the sugar moiety is composed of glucose residue only.

ii. Non-reducing terminus of sugar moiety being α-D-glucose

It was found that the glycopeptide of the present invention has a characteristic of bonding to concanavalin A (Con A). It is well known the Con A has a property of reacting selectively with polysaccharide which has any of α-D-glucose, α-D-mannose, or β-D-fructofuranosyl unit in its non-reducing terminus so as to produce precipitates. In view of this fact and the results of the item i, it was decided that the glucose in non-reducing terminus of the sugar moiety is α-D-type.

iii. sugar moiety consisting of three glucose residues

Figure 2:
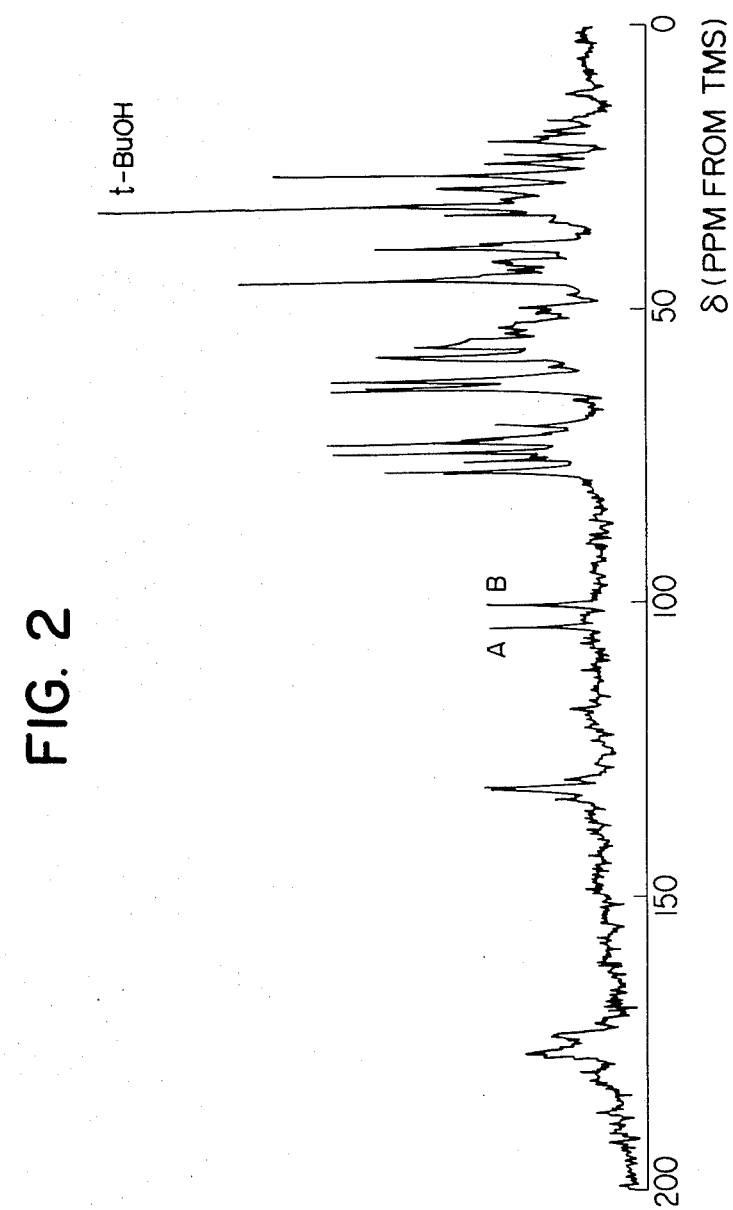
FIG. 2 is a $^{13}C$ NMR spectrum of the glycopeptide of the present invention.

The glycopeptide was analysed by $^{13}$C NMR spectrometory using t-butyl alcohol as internal standard (solvent: D$_2$O). FIG. 2 shows $^{13}$C NMR spectrum thus obtained.

According to J. B. STOTHERS, "Carbon-13 NMR Spectroscopy" Academic Press, New York, (1972), Chap. 11 and E. BREITMAIER and W. VOELTER, "$^{13}$C NMR Spectroscopy", Methods and Applications, Verlag Chemic Weinheim, Germany, (1974), Chap. 5, it is well known that the chemical shift range of carbon C(1) in glucose and its analogues, which is bonded to two oxygen atoms, is 110–90 PPM (PPM from TMS) and that of carbons C(2)–C(6) which are bonded to one oxygen atom, is 85–60 PPM.

It is evident from the studies of the intensities of the signals in the region of 110–60 PPM that the number of carbon of the sugar moiety is less than 24. This indicates that the number of sugar residue in the sugar moiety is 3 or 4, because one glucose ring has six carbon atoms and there may be some possibilities that the signals of other carbons in the peptide moiety of the glycopeptide are in this region.

The glycopeptide has only two peaks A (104.2 PPM) and B (100.2 PPM) in the region of the chemical shifts of carbon (1) in glucose ring. The intensities of these two signals are almost the same with each other. This fact eliminates the possibility of the presence of four glucose residues in the glycopeptide. Accordingly, it is evident that the sugar moiety is composed of three glucose residues.

iv. sugar moiety having bond pattern of gluα-1.6 gluβ-1.6 gluα

In order to assign the signals of carbons in the sugar moiety of the glycopeptide, $^{13}$C NMR spectra of 27 kinds of analogous sugars and their derivatives were measured at almost the same condition. From the analyses of these $^{13}$C NMR spectra, it has become evident that the signal B (100.2 PPM) (see FIG. 2) can be assigned to the carbon (1) of α-1,6 glucose-glucose linkage, because the observed chemical shift of isomaltose (α-1,6 linkage) (100.5 PPM) is very close to that of B. However, the signal A (104.2 PPM) cannot be immediately assigned, because any peaks of analogous sugars are not so close to that of A. As the chemical shifts of one glucose ring are influenced by the type of linkage of the second and/or the third glucose ring, substituent effects by the glucose ring on the chemical shifts were obtained by the detail analyses of the chemical shifts of glucose-glucose chain compounds with α-, β-1,1-, 1,2-, 1,3-, 1,4-, and 1,6-linkages. Using the values of the substituent effects and the chemical shifts of glucose thus obtained, expected chemical shifts of many types of combinations of three glucose rings were calculated. Thus, following five types were chosen as the appropriate combinations to fit the two peaks A and B or the glycopeptide from the analyses of C(1) chemical shifts.

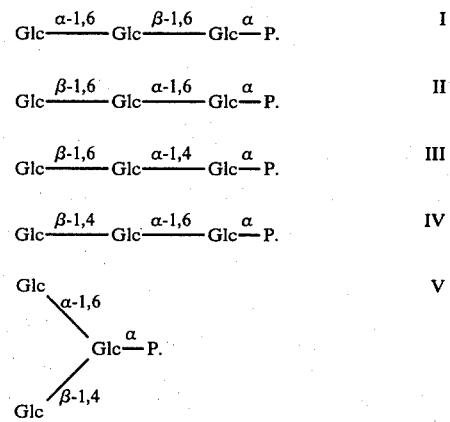

In the analyses of the chemical shift range of 85–60 PPM, it is expected that the chemical shift of the bonded carbon at 4-position of glucose of β-1,4 linkage must be near 81.4–81.2, considering the experimentally obtained value of cellobiose (β-1,4 linkage) (81.2 PPM) and the results of the calculations. However, such a signal cannot be found in the spectrum of the glycopeptide. The chemical shift of its nearest peak is 77.7 PPM, but it is too far. Therefore, types III, IV and V are excluded.

Moreover, from the Concanavalin A test, it has been made clear that the non-reducing terminus glucose in the glycopeptide has an α-configration. This and $^{13}$C NMR analyses indicate that the sugar moirty has α-1,6-β-1,6-α chain configration.

v. peptide moiety linking to sugar moiety through N-glycoside bond

According to the method of hydrolysis with strong alkali which is utilized ordinarily for destroying N-glycoside bond between asparagine or glutamine and sugar [Lee, Y. C. and Scocca, J. R. "J. Biol. Chem." 247, 5753–5758, (1972)], the glycopeptide of the present invention was hydrolized. Most of the products were trisaccharide (this corresponds with the fact described in the item iii).

Moreover, with respect to $^{13}$C NMR, a methine carbon which is bonded to one oxygen atom and one nitrogen atom (—O—CH—N<) is expected to resonate at much higher field (probably in the range of 85–70 PPM) than that bonded to two oxygen atoms. Taking this and only two signals with the same intensities for C(1) into account, it can be said that the sugar moiety has an N-glycoside linkage at C(1) of the terminal glucose, instead of the peptide linkage through a glucosamine.

From these facts, it is clear that the sugar moiety links to the peptide moiety through N-glycoside bond.

In view of the facts mentioned in the items i–v, it was concluded that the structural formula of the sugar moiety is as follows.

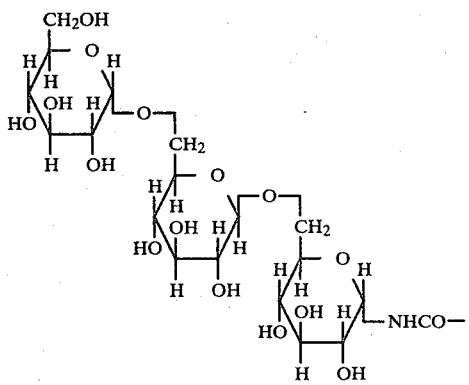

Now, the process of isolating the glycopeptide will be detailed hereinafter.

The GBM prepared according to Krakower and Greenspon's method is digested with a protein-digesting enzyme such as trypsin or collagenase and centrifuged. The obtained supernatant liquid is digested with pronase, and is centrifuged. The obtained supernatant liquid is dialyzed to remove dialyzable disaccharide (corresponding to Spiro's sugar peak 2). The remaining non-dialyzable solution is lyophilized. Thus obtained powder is dissolved to water and trichloroacetic acid is added to the solution to form precipitates which are removed by centrifuging. Since trichloroacetic acid has a characteristic of removing selectively glycopeptide containing mannose as sugar component as well as well known characteristic of reacting with free protein to form precipitates, Spiro's heteropolysaccharide (corresponding to the right sugar peak in FIG. 5 mentioned above) can be removed. Thereafter, the supernatant liquid is subjected to Con A affinity chromatography. As mentioned above, Con A has the characteristic of bonding to α-D-glucose in non-reducing terminus of polysaccharide. Accordingly, the glycopeptide of the present invention is trapped on Con A. Then the glycopeptide trapped on Con A is eluted with α-D-methyl mannose.

According to the inventor's study, since the glycopeptide has such characteristic that it is adsorbed selectively on non-water soluble material having negative charge, it is possible to utilize a step of contacting the supernatant liquid with the non-water soluble material and eluting the substance adsorbed on the non-water soluble material, in stead of the step of Con A affinity chromatography.

As the non-water soluble material having negative charge, it is able to use polymeric materials containing functional group having negative charge or inorganic materials having negative charge. The typical examples of the former are the materials having nitrile group, carboxyl group, sulfonic acid group or halogen atom, prepferably polyvinyl chloride, polyacrylonitrile, cellulose and cotton. The typical examples of the latter are porous glass, zeolite, silica gel, and sellite.

The optimum condition in the step of adsorbing is depend on the type of non-water soluble material, especially it is preferable to carry out at pH ranging from neutral to slight acidic.

As eluting solvent, it is able to use weak alkaline aqueous solution such as diluted ammonia aqueous solution, or aqueous solution of electrolyte such as sodium chloride or an agent for modifying protein such as urea.

According to the inventor's study, since the glycopeptide is present also in organs other than kidney, such as lung, aorta, liver, spleen, heart and muscle, it is possible to use these organs as a starting material.

According to the inventor's another study, since the glycopeptide is present in urine from human being, it is able to isolate the glycopeptide starting from urine from healthy males preferably.

In this case, the urine is firstly contacted with non-water soluble material. The adsorbed substance is eluted after washing of the non-water soluble material with distilled water. It is able to carry out the adsorption with good efficiency by concentrating previously the urine according to usual method, such as, for example, concentration under reduced pressure, concentration with ultrafiltration or foaming concentration.

It is preferable to regulate the urine at pH ranging from neutral to slight acidic. In this case, it is also able to use as eluting solvent weak alkaline aqueous solution or aqueous solution containing electrolyte or agent for modifying protein.

Thus obtained eluate is digested with pronase and is centrifuged. The supernatant liquid is dialyzed. The remaining non-dialyzable substance is treated with trichloroacetic acid and the produced precipitates are removed by centrifuging.

If necessary, the obtained supernatant liquid is further subjected to Con A affinity chromatography and the substance trapped on the Con A is eluted with an eluent.

The nephritogenicity of the glycopeptide will be described hereinafter.

Figure 3:
FIG. 3 is a microscopic photography showing renal tissue of rat after 8 months from an injection of the glycopeptide.
Figure 4:
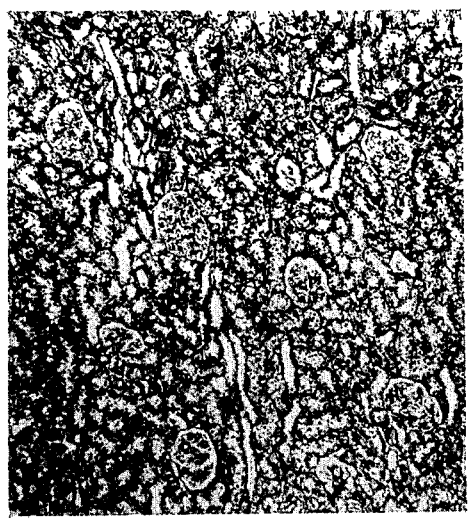
FIG. 4 is a microscopic photography showing renal tissue of normal rat.

In animals which received a single footpad injection of the glycopeptide with Freund's incomplete adjuvant, proteinuria began to appear 3-4 weeks after the injection and increased gradually. Morphologic changes of proliferative glomerulonephritis appeared 1.5 months after the injection and progressed, 6 to 8 months after injection, to typical chronic glomerulonephritis (the contracted kidney). FIG. 3 shows lesional organ of kidney after 8 months from the injection. It is found from the comparison with normal kidney (shown in FIG. 4) that the morphologic changes in kidney have progressed to typical chronic glomerulonephritis.

Furthermore, as the result of disorders of clinical metabolism, unique uremic osteodystrophy (a bone disease secondary of chronic renal failure) was produced in animals: that is, severe osteodystrophy was induced, 300-400 days after the footpad injection in these animals, with marked (over 10 fold) hyperplasia of the parathyroid gland and the decrease of serum Ca level.

The reproducing efficiency of nephritogenicity of the glycopeptide is almost 100%.

The present invention will be understood more readily by referenced to the following examples; these examples are intended to illustrate the invention and are not to be constructed to limit the scope of the invention.

Some of the examples relate to the isolation using organs excised from rat. However, it is possible, of course, to use equally as starting material the organs excised from animals other than rat, such as, for example, bovine, dog, rabbit, mouse, etc.

EXAMPLE 1

Isolation from rat GBM

Kidney excised from 1200 rats was washed fully with physiological salt solution under reflux to remove blood and thereafter was cut finely to collect renal cortex [Yield: about 1 kg (wet weight)].

The GBM was prepared from the renal cortex according to Krakower and Greenspon's method. More detailedly, the renal cortex was cut finely and separated with sieves having 150 mesh and 100 mesh and finally 170 mesh. The glomerulus remaining on the sieve having 170 mesh was washed fully with physiological salt solution and was subjected to treatment with super sonic wave. After washing with physiological salt solution many times and then with distilled water, the solution containing destroyed glomerulus was centrifuged at low speed. Pure GBM 20 g (wet weight) was obtained as precipitate.

The GBM was dissolved to small amount of phisiological salt solution adjusted to pH 8.0 with 0.1 M sodium borate. Trypsin was added in the amount of 0.5% of the weight of GBM and the mixture was incubated at 37° C. for 3 hours. The mixture was heated at 60° C. for 30 min. to inactivate trypsin and was centrifuged at 27,000 rpm for 35 min. The supernatant liquid was lyophilized.

The powder was dissolved to small amount of physiological salt solution and the mixture was adjusted to pH 7.8 with Tris acetate buffer and was digested with pronase. This enzyme was added initially in the amount of 0.3% with further enzyme additions of 0.1% at 24 and 48 hours. This incubation was carried out for a total period of 72 hours at 37° C. Thereafter, the undigested material was removed by centrifugation and the obtained supernatant liquid was lyophilized.

The powder was dissolved to distilled water. The solution was charged into cellulose tube (Visking tube, 27/32 inch) and the cellulose tube was dipped into the flowing water. The dialysis was continued for 3 days. In this way, dialyzable disaccharide was removed.

Trichloroacetic acid was then added to the nondialyzable materials in the amount of 5% and the mixture was stood still for short time. The produced precipitates were removed by centrifuging at 3,000 rpm for 30 min., whereby heteropolysaccharide was removed.

The obtained supernatant liquid was fed to a column fulfilled with Con A. After washing the column with distilled water, the substance trapped on the Con A was eluted with α-D-methyl mannose. The eluate was lyophilized so as to obtain the glycopeptide (10 mg).

It was confirmed by $^{13}C$ NMR analysis that the glycopeptide obtained by the process mentioned above has two signals at 104.2 PPM and 100.2 PPM.

EXAMPLE 2

Isolation from rat renal cortex

The renal cortex about 1 kg (wet weight) treated similarly to Example 1 was separated with a sieve having 9 mesh. The renal cortex which passed through the sieve was washed with small amount of physiological salt solution and then was dialyzed and lyophilized after desalting. The powder was dissolved to water and adjusted at pH 8.0 with 0.1 M sodium borate.

The preparation of the glycopeptide was carried out using this solution as a starting material similarly to Example 1. The glycopeptide was obtained with yield of 6-8 mg.

EXAMPLE 3

Isolation from rat lung

The lung excised from rat was washed fully with physiological salt solution under reflux in order to remove blood. The lung was cut finely and put into acetone. The lung tissue precipitating in acetone was collected and dried after removing acetone. Then, the powder was separated with a sieve having 9 mesh to remove bronchus.

Thus obtained lung tissue 200 g (dry weight) was used as a starting material. The preparation was carried out similarly to the Example 1. The glycopeptide was obtained with yield of 10 mg.

EXAMPLE 4

Isolation from rat aorta

The aorta excised from rat was put into acetone. After some days, acetone was removed and the aorta was dried and was milled with a mortar. Thus obtained aorta tissue 120 g was used as a starting material.

The preparation of glycopeptide from aorta tissue was carried out similarly to the Example 1. The glycopeptide was obtained with yield of 10 mg.

EXAMPLE 5

Isolation from rat liver

The liver excised from rat was washed fully with physiological salt solution under reflux to remove blood and then homogenized. The homogenate was centrifuged at 8,000 rpm to collect precipitates.

The isolation of glycopeptide was carried out using the precipitates 1,000 g (wet weight) similarly to the Example 1. The glycopeptide was obtained with yield of 5 mg.

EXAMPLE 6

Isolation from rat spleen

Using spleen excised from rat, the starting material was prepared similarly to the Example 5.

The isolation of glycopeptide from the starting material 1,000 g (wet weight) was carried out similarly to the Example 1. The glycopeptide was obtained with yield of 2-3 mg.

EXAMPLE 7

Isolation from rat heart

In this case, the homogenate prepared by homogenizing heart excised from rat was used as a starting material.

Using the homogenate 1,000 g, the isolation of glycopeptide was carried out similarly to the Example 1. The glycopeptide was obtained with yield of 6 mg.

EXAMPLE 8

Isolation from rat muscle

Using rat muscle, the starting material was prepared similarly to the Example 5.

The isolation of glycopeptide from this starting material 1 kg was carried out simialrly to the Example 1. The glycopeptide was obtained with yield of 2 mg.

EXAMPLE 9

The preparation of glycopeptide from rat GBM was carried out as shown in the Example 1 but, in stead of the step of Con A affinity chromatography, the step of adsorption with non-water soluble material was utilized in order to extract selectively the glycopeptide. More detailedly, the supernatant liquid obtained after the treatment with trichloroacetic acid was fed to the column fulfilled with sellaite. After washing the sellaite with distilled water, the glycopeptide adsorbed on the sellaite was eluted with ammonia aqueous solution. The eluate was neutralized and lyophilized after desalting. Whereby, the glycopeptide was obtained with yield of 10 mg.

It was confirmed by $^{13}$C NMR analysis that the obtained glycopeptide has two signals at 104 PPM and 100 PPM.

In the operation mentioned above, even if polyacrylonitrile fiber, polyvinyl chloride, cellulose, cotton, porous glass, zeolite, or silica gel is used in stead of sellaite, it is able to obtain equal results.

EXAMPLE 10

Isolation from human urine

Urine 1,000 l from healthy males was concentrated by feeding air into urine for 2 hours and then adding small amount of octanol to the produced foam. In this way, the concentrated urine 100 l was obtained. The concentrated urine was diluted with distilled water 100 l and was adjusted to pH 6.5. To this solution, sellaite 100 l was added and the mixture was agitated for 1 hour. Thereafter, the sellaite was collected by filtration. The separated sellaite was washed with alkaline water. The substance adsorbed on the sellaite was then eluted with alkaline solution containing sodium chloride. The eluate was neutralized and lyophilized after desalting with superfiltration and concentrating. The dry urine powder 2 g was obtained.

The powder was dissolved to small of physiological salt solution and the mixture was adjusted to pH 7.8 with Tris acetate buffer and digested with pronase. This enzyme was added initially in the amount of 0.3% and further in the amount of 0.1% at 24 and 48 hours. This incubation was carried out for a total period of 72 hours at 37° C. Thereafter, the undigested material was removed by centrifugation and the obtained supernatant liquid was lyophilized.

The powder was dissolved to distilled water. The solution was charged into cellulose tube (Visking tube, 27/32 inch) and the cellulose tube was dipped into the flowing water. The dialysis was continued for 3 days. In this way the dialyzable disaccharide was removed.

Trichloroacetic acid was added to the remaining non-dialyzable materials in the amount of 5% and the mixture was stood still for short time. The produced precipitates were removed by centrifuging at 3,000 rpm for 30 min. The obtained supernatant liquid was lyophilized (yield of 10–15 mg).

In order to obtain the glycopeptide having higher purity, the supernatant liquid after the treatment with trichloroacetic acid was fed to a column fulfilled with Con A. After the column was washed with distilled water, the substance trapped on the Con A was eluted with α-D-methyl mannose. The eluate was lyophilized.

It was confirmed by $^{13}$C NMR analysis that the glycopeptide from human urine also has two signals at 104 PPM and 100 PPM.

EXAMPLE 11

The concentrated urine 100 l obtained by the treatment same to that in the Example 10 was adjusted to pH 5.5 and then fed gradually to a column fulfilled with polyacrylonitrile fiber 300 g. After the polyacrylnitrile fiber was washed fully with water, the substance adsorbed thereon was eluted with 4% ammonia aqueous solution. The eluate was neutralized and treated similarly to the Example 10 so as to obtain dry urine powder 2 g.

The isolation of glycopeptide from the urine powder was carried out similarly to the Example 10. The glycopeptide was obtained with yield of 10–15 mg.

Example 12

Using polyvinyl chloride in stead of polyacrylonitrile fiber, the dry urine powder 2 g was obtained similarly to the Example 11.

The isolation of glycopeptide from the dry urine powder was carried out similarly to the Example 10 (Yield: 10–15 mg).

EXAMPLE 13

Human urine 1,000 l was adjusted to pH 7.5. After the produced precipitates were removed, the urine was fed at speed of 500 cc/min. to the column fulfiled with silica gel 30 l which was previously washed with 5% HCl and 10% NaCl aqueous solution. Thereafter, the column was wahsed with water and the substance adsorbed on the silica gel was eluted with 4% ammonia aqueous solution 4 l. The eluate was neutralized with HCl and was concentrated and finally lyophilized so as to obtain dry urine powder 4 g.

The isolation of glycopeptide from dry urine powder was carried out similarly to the Example 10 (Yield: 20–25 mg).

EXAMPLE 14

Human urine 1,000 l was fed at speed of 200 l/hour to a column (diameter 6 cm; height 30 cm) fulfilled with porous glass 1 l having mesh size of 120–200 mesh. Thereafter, the column was washed with water 10 l and the substance adsorbed on porous glass was eluted with 4% ammonia aqueous solution 4 l. The eluate was neutralized with 5% HCl and was concentrated and finally lyophilized so as to obtain dry urine powder 4.5 g.

The isolation of glycopeptide from the dry urine powder was carried out simialrly to the Example 10 (Yield: 20–25 mg).

The nephritogenicity of glycopeptide obtained in the examples mentioned above will be illustrated by the following experiments.

EXPERIMENT 1

The glycopeptide isolated from rat GBM (Example 1) was injected to footpad of rat with Freund's incomplete adjuvant. The injection amount of glycopeptide was 300–500 μg. After 8 months from the injection the rat was killed and dissected. It was confirmed that morphologic changes of kidney progressed to the contracted kidney which is a typical change of chronic glomerulonephritis.

EXPERIMENT 2

The glycopeptide (300–500 μg) isolated from rat lung (Example 3) was injected to footpad of rat. After 8 months from the injection, it was confirmed that morphologic changes of kidney progressed to the contracted kidney.

When the glycopeptide isolated from other organs, that is, aorta, liver, spleen, heart or muscle was injected to rat, the morphologic changes were the same to those observed in the case of GBM or lung.

EXPERIMENT 3

The glycopeptide (300–500 μg) isolated from human urine (Example 10) was injected to footpad of rat. After 8 months from the injection, it was observed that morphologic changes of kidney progressed to the contracted kidney.

EXPERIMENT 4

The glycopeptide (300–500 μg) isolated from rat GBM was injected to dog with Freund's incomplete adjuvant. Similarly to the case of rat, after 8 months from the injection, the morphologic changes of kidney progressed to the contracted kidney.

While the described embodiment represents the preferred form of the present invention, it is to be distinctly understood that the invention is not limited thereto but may be otherwise variously embodied within the scope of the following claims.

What is claimed is:

1. A process of isolating a glycopeptide consisting of a sugar moiety having a structural formula

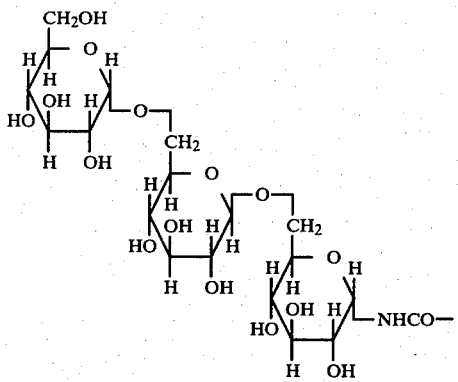

and a peptide moiety linking to the sugar moiety through N-glycoside bond, comprising steps of (1) digesting an organ of normal animal with a protein-digesting enzyme and centrifuging, of (2) digesting the supernatant liquid obtained in the step (1) with pronase and centrifuging, of (3) dialyzing the supernatant liquid obtained in the step (2), of (4) treating the non-dialyzable substance with trichloroacetic acid and centrifuging, and of (5) contacting the supernatant liquid obtained in the step (4) with non-water soluble material having negative charge and eluting the substance adsorbed on the non-water soluble material,
wherein said peptide moiety is one obtained from said organ of normal animal which is selected from the group consisting of kidney, lung, aorta, liver, spleen, heart and muscle.

2. The process claimed in the claim 1 wherein the non-water soluble material having negative charge is a polymeric material containing a functional group having negative charge, or an inorganic material having negative charge.

3. The process claimed in the claim 2 wherein the polymeric material is the one containing nitrile group, carboxyl group, sulfonic acid group or halogen atom.

4. The process claimed in the claim 3 wherein the polymeric material is polyvinyl chloride, polyacrylonitrile, cellulose, or cotton.

5. The process claimed in the claim 2 wherein the inorganic material having negative charge is porous glass, zeolite, silica gel or sellaite.

6. A process of isolating a glycopeptide consisting of a sugar moiety having a structural formula

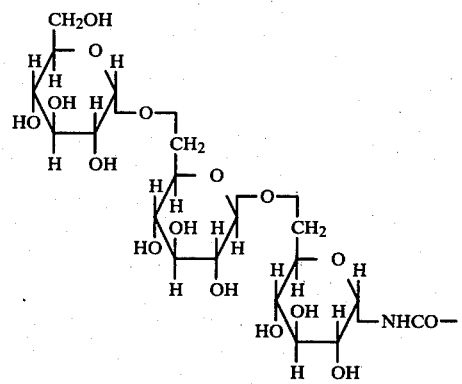

and a peptide moiety linking to the sugar moiety through N-glycoside bond, comprising steps of (1) contacting urine from healthy human being or the concentrate thereof with non-water soluble material having negative charge and eluting substance absorbed on the non-water soluble material, of (2) digesting the eluate with pronase and centrifuging, of (3) dialyzing the supernatant liquid obtained in the step (3), of (4) treating the non-dialyzable substance with trichloroacetic acid and (5) separating the supernatant containing glycopeptide from the precipitate formed in step (4).

* * * * *